United States Patent
Stoltz

(10) Patent No.: US 6,251,369 B1
(45) Date of Patent: *Jun. 26, 2001

(54) DENTAL FLUORIDE FOAM

(76) Inventor: Edwin I. Stoltz, 5716 Willow Creek La., Delray Beach, FL (US) 33484

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/174,774

(22) Filed: Oct. 19, 1998

Related U.S. Application Data

(63) Continuation-in-part of application No. 08/611,205, filed on Mar. 5, 1996, now Pat. No. 5,824,289.

(51) Int. Cl.[7] ............................................. A61K 7/18
(52) U.S. Cl. ................................. 424/45; 424/52
(58) Field of Search .................... 574/945; 424/52, 424/45

(56) References Cited

U.S. PATENT DOCUMENTS

| | | | |
|---|---|---|---|
| 3,527,219 | 9/1970 | Greenberg | 128/260 |
| 3,976,765 | 8/1976 | Nachtigal | 424/54 |
| 4,137,303 | 1/1979 | Gaffar et al. | 424/52 |
| 4,138,814 | 2/1979 | Weitzman | 32/14 B |
| 4,145,411 | 3/1979 | Mende | 424/45 |
| 4,310,510 | 1/1982 | Sherman et al. | 424/45 |
| 4,365,967 | 12/1982 | Guth et al. | 8/477 |
| 4,383,987 | 5/1983 | Kioz Peoplov | 424/49 |
| 4,410,508 | 10/1983 | Brown, Jr. et al. | 424/81 |
| 4,522,806 | 6/1985 | Muhlemann et al. | 424/52 |
| 4,528,182 | 7/1985 | Curtis et al. | 424/54 |
| 4,601,898 | 7/1986 | Stier et al. | 424/52 |
| 4,677,139 * | 6/1987 | Feinmann | 523/111 |
| 4,770,634 * | 9/1988 | Pellico | 433/217.1 |
| 4,808,388 * | 2/1989 | Beutler et al. | 514/941 |
| 4,844,902 | 7/1989 | Grohe | 424/449 |
| 4,871,531 | 10/1989 | Hartlaub et al. | 424/48 |
| 4,961,923 | 10/1990 | Heyde | 424/49 |
| 5,071,637 | 12/1991 | Pellico | 424/45 |
| 5,073,363 | 12/1991 | Pellico | 424/49 |
| 5,094,840 | 3/1992 | Isobe et al. | 424/50 |
| 5,736,158 * | 4/1998 | Quast | 424/464 |
| 5,824,289 * | 10/1998 | Stoltz | 424/45 |

* cited by examiner

Primary Examiner—Peter F. Kulkosky
(74) Attorney, Agent, or Firm—Steinberg & Raskin, P.C.

(57) ABSTRACT

Foamable dental fluoride compositions containing a water-soluble fluoride component in an amount sufficient to provide from about 0.5 to about 10% by weight available fluoride are disclosed. The compositions include an oil in water emulsion which is preferably dispensed in combination with an aerosol propellant to provide microcell-stable foam which exhibits enhanced foam retention properties. Methods of treating teeth with fluoride and methods of preparing the foam are also disclosed.

26 Claims, No Drawings

DENTAL FLUORIDE FOAM

CROSS REFERENCE TO RELATED APPLICATION

This application is a continuation-in-part application of U.S. patent application Ser. No. 08/611,205 filed Mar. 5, 1996 now U.S. Pat. No. 5,824,289.

BACKGROUND OF THE INVENTION

The use of fluoride to treat dental plaque is well documented. For example, fluoride is often added to community potable water supplies, consumer products such as rinses, gels, foams and, of course, toothpastes in order to reduce dental caries.

Over the years, various fluoride compounds such as sodium fluoride, stannous fluoride or sodium monofluorophosphate have been used to provide the beneficial activity required to reduce, inhibit, control and prevent dental plaque, and consequently, dental cavities, decalcification of tooth enamel. Professional dental practitioners often use fluoride gels and foams to affect a high degree of plaque control and prevention. Fluoride gels, however, have several shortcomings. For example, when gel-type products are applied with a toothbrush, patients often do not brush long enough to allow the fluoride to get into the interproximal and interdental spaces.

Fluoride gels are also applied by dental professionals using dental trays which fit over all of the upper or lower teeth at the same time and allow the gel to directly contact the teeth for periods of one to four minutes and optimize fluoride uptake by the tooth enamel. Although dental trays tend to be more effective than toothbrushes, currently available fluoride gels lack sufficient stability to remain in the oral cavity for the time period required for maximum therapeutic effect. The problem is especially critical when the dental tray with the gel is turned upside down to submerge the lower teeth in the fluoride-containing gel. In these situations, the gel quickly leaves the dental tray and reduces the effectiveness of the fluoride treatment is reduced.

One attempt to address the shortcomings of currently available products is set forth in U.S. Pat. No. 4,770,634. This reference discloses an aerosol, foamable fluoride product which can be dispensed into the trough of a dental tray. The patentees describe the foam as dense, stable and nonflowable. The compositions prepared in accordance with the '634 patent, however, also demonstrate the aforementioned physical stability problems, especially when used in dental trays which are turned upside down to treat the lower teeth. One of the chief drawbacks associated with these fluoride foams is that they are prepared using substantially all water-soluble ingredients. On the one hand, water-soluble and hydrophilic ingredients make preparing fluoride-based foams easy to formulate and which produce sufficient amounts of foam. On the other hand, the physical nature of such foam ingredients dictates that the foams and the foam cell structure will rapidly dissipate in the presence of (aqueous) saliva due to the inherent weak stability of a hydrophilic foam under acidic conditions and will fail to remain in intimate contact with the teeth for one to four minutes.

In the view of the foregoing, there is still a need for improved dental fluoride compositions, especially in the foam-type formulations. The present invention addresses this need.

SUMMARY OF THE INVENTION

It is an object of the present invention to provide improved foamable dental fluoride compositions.

It is a further object of the present invention to provide foamable dental fluoride compositions which demonstrate enhanced foam stability in the oral cavity.

A still further object of the present invention is to provide improvements in treating teeth with fluoride-based compositions.

Another object of the present invention is to provide a method of preparing foamable dental fluoride compositions which demonstrate enhanced foam stability in the oral cavity for time periods of four minutes or more.

These objects as well as others are achieved by the present invention which in one aspect includes a foamable dental fluoride composition containing an oil in water emulsion and a water-soluble fluoride component present in an amount sufficient to provide from about 0.5 to about 10% by weight available fluoride.

In preferred exemplifying embodiments, in order to maintain the lubricity of the composition during its production over a period of time, polyethylene glycol is added in an amount from about 1.0% to about 10.0% by weight. Also, to maintain the fluidity or solvency of the composition during its production, specially denatured alcohol may be added in an amount from about 2.0% to about 20.0% by weight. Both polyethylene glycol and specially denatured alcohol may be added to provide advantageous results.

In other particular aspects of this embodiment, the foamable dental fluoride composition includes:

a) from about 1.0 to about 10% by weight of an emulsifier;

b) from about 0.5 to about 5% by weight of an emulsion stabilizer; and c) from about 0.5 to about 3.0% by weight of a surfactant.

In still further preferred aspects of this embodiment the foamable dental fluoride compositions also contain:

d) from about 0.5 to about 5.0% by weight of a foam stabilizer; and/or e) an inorganic acid buffering agent.

The foamable dental fluoride compositions of the present invention include an emulsion which contains a combination of hydrophilic and hydrophobic ingredients. This combination also makes the fluoride foam more durable and demonstrate increased micro-cell stability in the oral cavity.

A further aspect of the present invention includes a method of preparing foamable dental fluoride compositions described above. The methods include:

a) preparing an oil in water emulsion containing a water-soluble fluoride component in an amount sufficient to provide from about 0.5 to about 10% by weight available fluoride; and b) combining the emulsion with an aerosol propellant to form a foamable dental fluoride composition.

The propellant and emulsion are preferably combined in an aerosol-type container. Suitable propellants include, for example, isobutane, propane and mixtures thereof.

Another aspect of the invention includes a method of treating teeth with a fluoride foam. This aspect of the invention includes dispensing a pressurized and foamable oil in water emulsion containing from about 0.5 to about 10% by weight available fluoride to form a fluoride foam and contacting the teeth with the dental foam, preferably in an acidulated medium, to effect fluoride uptake by the teeth. The methods of treatment take advantage of the increased oral cavity stability afforded by the foams described herein to provide enhanced fluoride uptake by the tooth enamel.

As a result of the present invention, there are provided stable foamable dental fluoride products which demonstrate significantly greater durability after being dispensed into dental trays and, more importantly, after the foam has been placed in the oral cavity where contact with patient saliva is unavoidable. Furthermore, the durable nature of the fluoride foams of the present invention allows the practitioner to be assured that a sufficient amount of fluoride is present to intimately act upon the dental enamel and allow therapeutic fluoride ion uptake.

For purposes of the present invention, the term "orally compatible" shall be understood to describe compositions and ingredients which are generally regarded as safe for use in the oral cavity.

For a better understanding of the present invention, together with other and further objects, reference is made to the following description and the scope of the present invention will be pointed out in the appended claims.

DETAILED DESCRIPTION OF THE INVENTION

The foamable dental fluoride compositions include oil in water emulsifiers and contain a water-soluble fluoride component which is present in an amount sufficient to provide from about 0.5% to about 10% by weight available fluoride. In preferred aspects of the invention, the water-soluble fluoride component of the foamable fluoride compositions is present in an amount which provides the composition with from about 0.5% about 5% available fluoride. Most preferably, the water soluble fluoride component is present in an amount which provides from about 1 to about 3% available fluoride. The water-soluble fluoride component can be selected from materials such as sodium fluoride, sodium monofluorophosphate, stannous fluoride and the like. Fluoroalkyl-phosphate salts such as monoamonium 1,1,7-trihydroperfluoroheptyl phosphate, described in U.S. Pat. No. 2,955,985 and/or quaternary ammonium fluorides such as doceyltrimethyl-ammonium fluoride, described in U.S. Pat. No. 3,124,512 are also of use. The disclosure of each of the foregoing patents is incorporated by reference herein. Mixtures of the foregoing fluorides such as combinations of sodium fluoride and one or more of the aforementioned ingredients are also contemplated. Other orally compatible water-soluble fluoride containing compositions not specifically mentioned but known to those of ordinary skill can also be included herein.

Sodium fluoride is particularly well suited for use in compositions of the present invention and can be present in the formulation in amounts ranging from about 1.1% to about 2.2% by weight so as to allow the foam to deliver the above-mentioned range of available fluoride. Preferably, the sodium fluoride will comprise from about 1.0% to 10% by weight and most preferably from about 2.0% to 6.0% by weight. Those of ordinary skill in the art will of course realize that the actual amount of water-soluble fluoride component in the composition will be greater than the amount of fluoride delivered and will vary according to the type of fluoride component used. The foam compositions of the present invention are based on the amount of available fluoride delivered by the component rather than by the weight of the ingredient.

One of the keys to the foams of the present invention is the fact that the foams are based on an oil in water (hydrophobic) emulsion rather than an aqueous or hydrophilic system. An emulsion is a dispersed system containing at least two immiscible liquid phases. In order for an emulsion to be stable, it must contain at least three components, i.e., the dispersed phase, the dispersion medium, and the emulsifying agent. Preferably, emulsions formed in accordance with the present invention are oil-in-water emulsions with the dispersed phase being an oil, dispersed as droplets throughout the aqueous dispersion medium. Suitable emulsifiers or emulsifying agents are discussed in detail below.

In preferred aspects of the invention, the oil-in-water emulsifying agents include combinations of cetyl phosphate and stearic acid such as that available from Croda, Inc. under the trade name CRODAFOS CP50. The emulsifying agents can also be added as individual components in ratios of cetyl phosphate to stearic acid ranging from about 1:4 to 4:1. This hydrophilic combination of ingredients is advantageously included in the dental foams of the invention and also contributes to maintaining the pH in the desired acidic range. For example, dental foams containing concentrations of about 2% of this hydrophobic emulsion combination result in foam pH's ranging from about 2.5 to about 3.5 which are desirable for acidulated fluoride foam products. Furthermore, this combination of ingredients can reduce or even eliminate the need to include separate acidulating agents such as phosphoric or citric acids which are often required in prior art dental foams. Alternative emulsifying agents can be selected from the non-limiting list including trideceth-7 carboxylic acid, Incrodet TD-7-C available from Croda, acid forms of ethoxylated fatty alcohols, oleth 3, oleth 5, oleth 10, oleth 20, steareth-10, celeth-20, mixtures thereof and the like. Thus, acidic emulsifying agents are preferred in some aspects of the invention to provide dental compositions with a pH of from about 2.5 to about 3.5.

The foregoing list of emulsifiers is to be regarded as illustrative and not limiting. Functionally equivalent emulsifying agents which are orally compatible are also contemplated for use herein. Preferably the emulsifier contributes to maintaining the desired acid pH range of the foam such as those containing acid (i.e. carboxylic) groups. The foamable dental fluoride compositions of the present invention preferably include from about 1.0% to about 10% by weight of an emulsifier; more preferably from about 1.0% to about 8.0% by weight; and most preferably from about 2.0% to about 4.0% by weight emulsifier.

The emulsions of the present invention also preferably include an emulsion stabilizer. A non-limiting list of suitable orally compatible emulsion stabilizers includes materials such as polyoxyethylene (3) oleyl alcohol phosphate, hereinafter "oleth-3 phosphate", also available from Croda, Inc. under the trade name CRODAFOS N3 acid, other phosphate ester-containing emulsion stabilizers such as CRODAFOS N10 acid (polyoxyethylene (10) oleyl alcohol phosphate) or "oleth-10" phosphate or CRODAFOS CAP, PPG-10 cetyl ether phosphate and related agents having relatively poor water solubility cetostearyl alcohol, stearyl alcohol, olelyl alcohol and related fatty alcohols with linear carbon chains and wax-like materials having high molecular weights, phosphated cetyl ether, i.e. crodafos CAP acid, behenic acid and mixtures thereof. Preferably, however, the emulsion stabilizer is oleth-3 or oleth- 10 phospate. The emulsion stabilizer is present in amounts of from about 0.5% to about 5% by weight of the dental compositions and preferably in an amount of from about 1.0% to 4.0% by weight. The phosphate-based agents are also preferable in view of their acid nature which serves to reduce or eliminate the need for separate acidulants such as phosphoric or citric acid in the foam formulation.

The dental compositions of the present invention can also include a surfactant that contributes to the emulsification of the hydrophobic emulsifier and emulsion stabilizer in the dental foam. The surfactants are preferably water-soluble and are useful in the aerosol fluoride foam products of the present invention to help lower surface tension in coupling all of the emulsion ingredients together and form a stable, oil-in-water emulsion that ultimately results in a dense fine cell foam. The surfactant also assists the propellant in forming the micro-cell structure with greater surface area and results in a stable foam product and in forming a shiny, continuous surface skin to the dispensed foam product.

The surfactant is present in amounts of from about 0.5% to about 3.0% by weight and preferably in amounts of from about 1.0% to 2.0% by weight. A non-limiting list of surfactants includes sodium N-methyl-N-cocoyl taurate, known in the trade as Adinol CT95, or sodium methyl cocoyl taurate, known as Geraphon TC-270, both available from Rhone Poulenc Chemicals of Cranbury, N.J., and other surfactants such as N-coco-beta-aminobutyric acid, monosodium-N-lauryl- 1-glutamate, monosodium-N-cocoyl- 1-glutamate and mixtures thereof. The foregoing list of surfactants is to be regarded as illustrative and not limiting. It will be appreciated that a wide variety of orally compatible anionic and nonionic surfactants can be used in the compositions of the present invention. Preferably, however, the surfactant is sodium N-methyl N-cocoyl taurate. The surfactants selected for use in the compositions of the present invention are preferably of the foaming type since the emulsion ingredients and adjunct ingredients such as emulsion stabilizers are not associated with foaming action and are not very soluble in water.

The foamable dental fluoride compositions of the present invention can also include a foam stabilizer. A non-limiting list of orally-compatible foam stabilizers includes materials such as cetyl alcohol, USP/NF, also known as 1-hexadecanol, available from Rhone Poulenc Chemicals Parsippany, N.J., sodium monostearate, cocoamide DEA (diethanolamine), lauramide DEA, polypropylene glycol-14-butyl ether and mixtures thereof Preferably, the foam stabilizer is cetyl alcohol, USP/NF. The compositions of the present inventions can include the stabilizer in amounts of from about 0.5% to about 5.0% by weight and preferably in amounts of from about 1.0% to about 2.5% by weight.

The compositions of the present invention can also include an orally compatible inorganic acidic buffering agent to facilitate and enhance fluoride uptake by the teeth dental enamel. Suitable acidic buffering agents include, without limitation, phosphoric or citric salts, inorganic acidulants such as sodium monophosphate USP and mixtures thereof. In preferred aspects of the invention where acidic emulsifying agents are included, inorganic acidulants such as monosodium phosphate, are included in amounts sufficient to buffer and maintain the pH of the dental foams in the preferred acid range of about 3.0 to about 4.5.

The foamable dental fluoride compositions of the present invention can also include ancillary ingredients to provide commercially acceptable products. Such ingredients will be apparent to those of ordinary skill in the art. For example, it is contemplated that the foamable compositions will include preservatives such as sodium benzoate, sweetening agents such as sodium saccharin, flavorants, colorants and other accessories.

In another aspect of the invention, there are provided methods of preparing the foamable dental fluoride compositions described herein. The methods include:

a) preparing an oil in water emulsion concentrate containing a water-soluble fluoride component in an amount sufficient to provide from about 0.5% to about 10% by weight available fluoride; and b) combining the emulsion concentrate with an aerosol propellant to form a foamable dental fluoride composition.

The compositions of the present invention can be prepared in the following general manner. Those of ordinary skill in the art will realize that modifications can be made to the foregoing illustrative procedure without departing from the steps necessary for forming a foamable fluoride containing emulsion. For example, the temperatures set forth below will vary somewhat depending on the particular ingredients selected. One compounding procedure includes the following steps:

Step 1. The prescribed quantity of water is charged into a stainless, scale mounted batch tank which is equipped with a heat source and mixer. The water is heated to a temperature which is conducive for adding the emulsion ingredients, i.e. over about 130° F. (54° C.), before the addition of any non-water soluble ingredients.

Step 2. Using moderate mixing speeds, the emulsifier ingredients, i.e. the cetyl phosphate and stearic acid in flake form, are slowly added to the mixing/heating batch tank. In this particular illustration, the compounder maintains the batch temperature below about 150–160° F. (65–72° C.).

Step 3. The emulsion stabilizer, e.g. oleth-3 phosphate, in its required weight per the formula is then added to the batch tank containing the emulsion concentrate mix ingredients. In the case of oleth 3, the batch temperature should be close to about 150–160° F. (65–72° C.) during addition.

Step 4. Next, the foam stabilizer, such as 1-hexadecanol USP/NF or cetyl alcohol, is added to the batch tank containing the emulsion concentrate ingredients. In the case of cetyl alcohol, the foam stabilizer is added with the batch ingredients at a temperature of about 150–160° F. (65–72° C.) and held constant.

Step 5. The surfactant is added. For example sodium N-methyl N-cocoyl taurate is slowly sifted into the batch vortex and the batch is allowed to mix for about 15–30 minutes before being sampled for undissolved ingredients.

Step 6. Once it has been established that all the ingredients are finally in solution, mixing is continued and the heat is reduced to allow the addition of the acidic buffering agent, i.e. sodium monophosphate.

Step 7. The balance of the ingredients, i.e., sodium fluoride, sweeteners such as saccharin, flavoring agents, preservatives, colorants, if desired, as well as specially denatured alcohol (e.g., SDA 38B) and polyethylene glycol (PEG) if used, are added when the batch temperature reaches about 110–115° F./ 43–46° C. or slightly lower. The moderate speed mixing is continued while maintaining the concentrate temperature in the range of about 100–110° F./ 37–43° C. throughout the can filling operation.

The batch concentrate is kept under constant mixing during the fill process when it is combined with a propellant and packaged into containers. The batch concentrate is then added in predetermined amounts to an appropriate container. For example, the emulsion-based concentrate can be added to an open-mouth aerosol container to which an aerosol valve without a dip tube is attached to the 1" opening and then mechanically crimped in place to form a leak-proof, hermetically sealed package. The container is then charged through the valve stem with an aerosol propellant to a predetermined operating pressure before the container is fitted with a dispensing actuator and spout assembly if required on the valve. In use, the aerosol containers containing the foamable pressurized emulsion concentrate can be shaken and the actuator engaged to release a sufficient amount of fluoride foam into a dental tray trough. One suitable aerosol container is an aluminum tube to which a special aerosol valve is crimped into place for a hermetically sealed package. Such cans are inverted prior to use in order to dispense the foam. To facilitate dispensing the fluoride foam, the aerosol valve can also have an elongated nozzle type actuator that precisely directs the product into the dental tray.

As noted above, the composition ingredients used for the fluoride foam concentrate are not easily soluble in water. Thus, in order to achieve a concentrate that does not have any undissolved particulate matter, relatively high heat combined with mixing is used to achieve a milky white homogeneous liquid emulsion which would not be generally possible if the formulation was compounded or batched at ambient or room temperature.

The aerosol propellant selected for inclusion in the products of the present invention will have an effect on the cell structure and physical stability of the resulting foam product. It is also preferable to use propellants that are non-ozone depleting such as the well known hydrocarbon propellants n-butane, isobutane, propane and mixtures thereof. The aerosol industry has designated these propellants with a numerical designation that identifies its vapor pressure measured in pounds per square inch gauge (psig). Thus, a propellant listed as A-17 is n-butane (17 psig). Likewise, isobutane is called A-31 (31 psig).

In order to prepare the foamable compositions described herein, it has been determined that relatively high pressure propellants are preferable in order to form foams having sufficient microcell structure with sufficient stability. Therefore, propellants having a vapor pressure of about 40 psig or greater are preferred. One useful propellant is propellant A-46 (46 psig), a blend of isobutane/propane (84.5%/15.5% by wt). More preferably, the propellants included herein have a vapor pressure of from about 60 psig to about 70 psig. Such propellants, when combined with the emulsion-based concentrate produce exceptional, stable microcell foams. Within this aspect of the invention, propellants such as Propellant A-60, a blend of isobutane/propane (69.0%/31.0%, by wt) having a vapor pressure of 60 psig and Propellant A-70, a blend of isobutane/propane (57.0%/43.0% by wt) having a vapor pressure of 70 psig can be used. High pressure propellants produce micro-cell foams that have greater surface area for stronger, more durable foams than the macrocell foams produced with low pressure propellants. Thus, the higher pressure propellants allow the use of less propellant in the final composition. For example, foams usually requiring 6.0% to 10.0% by weight A-31 can be made with 3.5% to 5.0% by weight A-60 or A-70. An additional advantage of using the A-60 or A-70 propellants is that the resulting foams are microcell stable foams that retain their physical form even when dispensed on a surface and inverted (i.e., a lower dental tray). A-60 is an optimum hydrocarbon propellant system to produce a stable, dense, microcell foam product.

The foregoing propellants are set forth for purposes of illustration and not exclusion. Those persons skilled in the art will realize that other aerosol propellants, alone or in combination with others, can produce sufficiently high vapor pressure and can also be included herein. The following table sets forth suitable alternative aerosol propellants which can be readily combined to form suitable blends with vapor pressures compatible with the foam systems described herein. For example, a blend of HCFC22:HCFC142b (40:60% by wt) provides a propellant blend with 65–70 psig vapor pressure.

| PROPELLANT | CHEMICAL NAME | VAPOR PRESSURE (psig) @ 70° F. |
|---|---|---|
| Dymel | dimethyl ether | 63 |
| HCFC-22 | chlorodifluoromethane | 121 |
| HFC-152a | 1,1-difluroethane | 63 |
| HCFC-142-b | 1,1,1-chlorodifluorethane | 29 |
| HFC-134a | 1,1,1,2-tetrafluorethane | 81 |

In another aspect of the invention, there is provided a method of treating teeth with a fluoride foam composition prepared in accordance with the present invention. The method includes dispensing an acidulated, pressurized and foamable oil in water emulsion containing a water soluble fluoride component in an amount sufficient to provide from about 0.5 to about 10% by weight available fluoride from a container to form a foam and contacting the teeth with the foam to effect fluoride uptake by the teeth. In preferred aspects of this embodiment, the pressurized composition is dispensed into the trough of a dental tray to form an acidic fluoride foam within the tray or a trough contained therein and the trough or dental tray containing the dental foam is arranged into engagement with the teeth to effect fluoride uptake by the teeth.

EXAMPLES

The following examples serve to provide further appreciation of the invention but are not meant in any way to restrict the effective scope of the invention.

EXAMPLE 1

The dental fluoride foam formulations of Examples 2–6 were made following the general procedure set forth below. In all examples, the sodium fluoride concentration was adjusted to reflect a final fluoride concentration of 1.23% wt (±10%). The ingredients listed as "inactives" include the sweetening, preservation, coloring and flavor ingredients. These ingredients have no bearing on the formation or stability of the resulting fluoride foam. The sum percentage by weight of all ingredients of this type are given as one figure. The foam formulations were also evaluated for foam weight and physical characteristics.

The compounding procedure follows:

Step 1. The prescribed quantity of water was charged into a stainless, scale mounted batch tank equipped with the proper heat source and mixer. The water was allowed to heat to over 130° F. before the first non-water soluble ingredient is added with moderate mixing speed.

Step 2. The hydrophobic emulsifier was weighed and the proper amount slowly added to the mixing/heating batch. The batch temperature is kept below 160° F.

Step 3. The hydrophobic emulsion stabilizer in its required weight per the formula was added to the concentrate mix with batch temperature kept close to 150° F.

Step 4. The non-water foam stabilizer was added to the concentrate batch with the temperature held constant at about 160° F.

Step 5. The surfactant was slowly sifted into the batch vortex and the batch was allowed to mix for 15–30 minutes.

Step 6. The concentrate was sampled to establish that all the ingredients are in solution. Thereafter, the mixture was mixed for an additional 15 minutes. The heat was reduced and mixing was continued.

Step 7. When the temperature was at 120–130° F., the correct amount of acidic buffering agent was added.

Step 8. The balance of the "inactive" ingredients were added when the temperature was at about 115–120° F.

Step 9. The active amount of fluoride was added with mixing before adding the flavorant and colorant.

Step 10. After about 15 minutes of mixing the concentrated batch was sampled to determine the fluoride content and pH at 77° F. The sampling was done from the bottom, middle and top of the concentrate.

Step 11. Once the target fluoride content 1.23±10% was verified, the batch was ready for liquid filling into aerosol cans. The batch is kept under constant mixing and at a temperature of about 90–100° F. during the entire can fill process.

Step 12. The aerosol value was placed on the filled aerosol can, crimped and pressure-filled through the stem with the specified propellant.

EXAMPLE 2

Using the procedure outlined in Example 1, a first foamable fluoride formulation was prepared according to the specific formula set forth below.

| Fluoride Foam Formulation #1: | %/WT. |
| --- | --- |
| Deionized Water | 89.908 |
| Cetyl phosphate-stearic acid | 2.080 |
| Oleth-3 phosphate | 1.040 |
| Sodium-N-methyl N-cocoyl taurate | 0.520 |
| Sodium fluoride, U.S.P. | 3.000 |
| Inactives: | 3.452 |
| Total: | 100.000 |

The formulation was then dispensed into aerosol containers. One portion of the fonnulation was combined with Propellant A-31 (isobutane) and the remaining portion was combined with Propellant A-70 isobutane/propane (57.0/ 43.0 wt %). The ratio of formulation to propellant is set forth below:

| Item | %/WT. | %/WT. |
| --- | --- | --- |
| Formulation #1 concentrate. | 91.4 | 96.5 |
| Propellant A-31 | 8.6 | — |
| Propellant A-70 | — | 3.5 |
| Totals: | 100.0 | 100.0 |

A representative sample of the foam from each aerosol container was then tested for foam condition and moisture loss after standing for twenty minutes at 72° F.

TEST RESULTS

Dispensed foam condition

A-31: Large, open, airy cell structure

A-70: Shiny surface, loose stability

| | Foam Weight (grams): | |
| --- | --- | --- |
| Item | Propellant A-31 | Propellant A-70 |
| Initial Foam weight | 1.32 | 2.15 |
| Ending Foam weight | 1.21 | 2.03 |
| Moisture weight loss | 0.11 | 0.12 |
| wt % Moisture Loss | 8.30 | 5.60 |

Discussion

The percentage of A-31 was more than twice that which was used for the A-70 propellant. It was observed that (1) the use of 8.6% A-31 propellant resulted in the formation of a light, unstable, large cell foam. (2) The actual weight of the foam dispensed was extremely light as compared to the A-70 dispensed foam. Both mounds of foam were physically similar in size. (3) The moisture loss, as calculated by wt %, of the A-31 foam was more than that of the A-70 foam (8.3 vs. 5.6%). Initially, the A-31 foam dispensed with airy, with large open cells. The A-70 foam had a shiny, continuous surface look and appeared to be more stable.

EXAMPLE 3

In this example, the procedure set forth in Example 2 was repeated using the formula set forth below. It will be noted that this formulation includes the additional ingredient cetyl alcohol.

Fluoride Foam Formulation #2

| Ingredient | %/WT. |
| --- | --- |
| Deionized Water | 88.868 |
| Cetyl phosphate-stearic acid | 2.080 |
| Oleth-3 phosphate | 1.040 |
| Sodium-N-methyl N-cococyl taurate | 0.520 |
| Cetyl alcohol | 1.040 |
| Sodium fluoride, USP | 3.000 |
| Inactives: | 3.452 |
| Total: | 100.000 |

The formulation was then dispensed into aerosol containers along with either Propellant A-31 or A-70 in the same manner as described above in Example 2.

Aerosol Fill

| Item | %/WT. | %/WT. |
| --- | --- | --- |
| Formulation Concentrate. #2 | 92.3 | 95.7 |
| Propellant A-31 | 7.7 | — |
| Propellant A-70 | — | 4.3 |
| Totals: | 100.0 | 100.0 |

TEST RESULTS

Dispensed foam condition

A-31: Light foam, good cell formation

A-70: Shiny, creamy continuous surface

| | Foam Weight (grams): | |
|---|---|---|
| Item | Propellant A-31 | Propellant A-70 |
| Initial Foam Weight | 1.65 | 2.58 |
| Ending Foam Weight | 1.54 | 2.48 |
| Moisture weight loss | 0.11 | 0.10 |
| wt % Moisture Loss | 6.7 | 3.9 |

Discussion

Formulation #2 is similar to Formulation #1 except that cetyl alcohol was added with the hope that it would provide foam stabilization and thereby result in better moisture retention. Unlike the A-31 based foam of formulation #1 which was airy and open, the A-31-based composition which included formulation #2 was a satisfactory small cell foam product and demonstrated that cetyl alcohol significantly stabilized both products containing formulation #2 and significantly reduced moisture loss in cases of both A-31 and A-70 propellant containing products. As was the case with formulation #1 (shown above in Example 2) the composition containing the A-70 propellant dispensed a much heavier, denser foam than that obtained with the A-31 foam. This was the case in this example even though visually the foam mounds were dimensionally alike.

EXAMPLE 4

The procedures of Example 2 were again repeated to produce Formulation #3 using the formula set forth below:

Fluoride Foam Formulation #3

| Ingredient | %/WT. |
|---|---|
| Deionized water | 87.308 |
| Cetyl phosphate-stearic acid | 2.600 |
| Oleth-3 phosphate | 1.040 |
| Sodium-n-methyl N-cocoyl taurate | 1.040 |
| Cetyl alcohol, U.S.P. | 1.560 |
| Sodium fluoride, U.S.P. | 3.000 |
| Inactives: | 3.452 |
| Total: | 100.000 |

The formulation was then dispensed into aerosol containers using the propellant A-31 as shown below:

Aerosol Fill

| Item | %/WT. | %/WT. |
|---|---|---|
| Formulation Concentrate. #3 | 90.6 | 96.1 |
| Propellant A-31 | 9.4 | — |
|  | — | 3.9 |
| Totals: | 100.0 | 100.0 |

TEST RESULTS

Dispensed Foam condition

A-31: Shiny, creamy skin surface,

A-70: Shiny, creamy skin surface

| | Foam Weight (grams): | |
|---|---|---|
| Item | Propellant A-31 | Propellant A-70 |
| Initial foam weight | 1.27 | 2.72 |
| Ending Foam weight | 1.18 | 2.60 |
| Moisture Weight loss | 0.09 | 0.12 |
| wt % Moisture Loss | 7.10 | 4.40 |

Discussion

In this Example, formulation #3 was prepared to include higher amounts of cetyl alcohol and the cetyl phosphate-stearic acid ingredients than that found in formulation #2. Again, pressurized samples of formulation #3 shown above were made with A-31 and A-70 propellants. In spite of the increased amounts of the ingredients, the results provided by the products including formulation #3 were similar in pattern to formulations #1 and #2. The initial foam dispensed with the A-31 product resulted in an acceptable product that had a shiny continuous surface indicating a foam with small cell structure. The A-70 foam was very similar having both the shiny and creamy looking surface also with no cell structure being visible. This foam also looked like a micro-cell foam due to both the composition ingredients and the relatively high vapor pressure of the A-70 propellant.

The foam dispensed using formulation #3 and A-31 propellant was relatively light weight (1.27 grams). After 20 minutes at 72° F., the foam had a 7.1 wt % loss. In the case of the foam product made with A-70, the pressurized foam produced an extremely heavy foam of 2.72 grams and a loss of only 4.4 wt % moisture after the 20 minutes test period. This was consistent with the results obtained with formulations #1 and 2. The use of relatively high pressure propellants from A-46 through A-70 hydrocarbon are therefore preferred and products made with propellants known as A-60 or A-70 are preferred to produce a dense, stable fluoride foam. Further, the use of the preferred hydrocarbon propellants can be used in smaller percentage by weight as compared to the lower A-31 and A-46 propellants.

EXAMPLE 5

Formulation #4

In this example, the beneficial foam properties obtained by adding a surfactant were demonstrated. Formulation #4 was prepared by eliminating the Sodium N-methyl N-cocoyl taurate from the foam product. The formula is set forth below:

Fluoride Foam Formulation #4

| Ingredient | %/Wt. |
|---|---|
| Deionized Water | 88.348 |
| Cetyl phosphate & stearic acid | 2.600 |
| Oleth-3 phosphate | 1.040 |
| Cetyl alcohol, U.S.P. | 1.560 |
| Sodium fluoride, USP | 3.000 |
| Inactives: | 3.452 |
| Total: | 100.000 |

Aerosol Fill

| Item | %/Wt. | %/Wt. |
|---|---|---|
| Formulation #4 Concentrate. | 92.1 | 95.7 |
| Propellant A-31 | 7.9 | — |
| Propellant A-70 | — | 4.3 |
| Totals: | 100.0 | 100.0 |

TEST RESULTS

Dispensed foam condition
A-31: Striated, non-continuous surface, open cells
A-70: Large open cells, loose

| Item | Foam Weight (grams): | |
|---|---|---|
| | Propellant A-31 | Propellant A-70 |
| Initial Foam weight | 1.65 | 3.48 |
| Ending Foam weight | 1.55 | 3.35 |
| Moisture weight loss | 0.10 | 0.13 |
| wt % Moisture Loss | 6.10 | 3.70 |

Discussion

Formulation #4 contained the same percentage of "active" ingredients as that set forth in Example 4 for formulation #3 except for the absence of Sodium N-methyl cocyl taurate which acts as a true surfactant in the final fluoride composition. As with the other formulations shown above, samples were made using both A-31 and A-70 aerosol propellants. The resulting foam products of formulation #4 did not contain as favorable foam structures in the case of both the A-31 and A-70 samples of formulations #2 and #3. It was noted that the absence of a surfactant, which aids in foaming, such as Sodium N-methyl cocyl taurate, caused unsatisfactory stable foams. As before, the A-31 sample resulted initially in an airy, light, open cell product. Upon standing for 20 minutes at 72° F. the A-31 foam lost 6.1% of its moisture content, by weight.

The A-70 sample of formulation #4 initially dispensed large airy cells also. While the dispensed foam was heavy, 3.48 grams, it did not look dense or stable. As before, the A-70 foams were heavier than the A-31 foams in all the test formulations shown above. The wt % moisture loss of the two propellant samples of formulation #4 were also consistent with the other formulations shown here.

EXAMPLE 6

Fluorede Foam Formulation #5

| Ingredient | %/Wt. |
|---|---|
| Deionized water | 84.100 |
| Cetyl $PO_4$ & stearic acid | 5.000 |
| Oleth-3 $PO_4$ | 3.000 |
| Sodium-methyl-cocoyl taurate | 1.200 |
| Cetyl alcohol, USP | 1.600 |
| Sodium monophosphate, USP | 1.000 |
| Sodium saccharin, NF | 0.500 |
| Sodium benzoate, NF | 0.100 |
| Sodium fluoride, USP | 3.000 |
| Flavor | 0.500 |
| Total: | 100.00 |

Aerosol Fill

| Item | %/Wt. | %/Wt. | %/Wt. |
|---|---|---|---|
| Formulation #5 Concentrate | 95.0 | 95.4 | 95.6 |
| Propellant A-31 | 5.0 | — | — |
| Propellant 70 | — | 4.6 | — |
| Dymel 22:142b (40:60%/wt) | — | — | 4.4 |
| Totals: | 100.0 | 100.0 | 100.0 |

TEST RESULTS

Dispensed Foam condition
Foam A-31; dull light, airy cells
Foam A-70-shiny stable, smooth microcell foam.
Foam Dymel Blend: shiny, stable microcell
Foam Weight (grams)

| Item | Foam A-31 | Foam A-70 | Dymel Foam |
|---|---|---|---|
| Initial | 1.93 | 2.53 | 3.58 |
| Ending Foam wt (g) | 1.80 | 2.46 | 3.50 |
| Moisture loss | 0.13 | 0.07 | 0.08 |
| wt % moisture loss | 7.20 | 2.80 | 2.30 |

TEST RESULTS

In this example, the role of another propellant which achieves a good stable micro-cell fluoride foam product was used. For this test, Dymel foam (HCFC 22:HCFC 142(b) (40:60% by wt.) blend was used that yields a vapor pressure of roughly 65–70 psig. The results are shown above.

As can be seen, a 5% by wt. concentration of A-31 in formulation #5 continues to show a high degree of moisture loss (7.2%) after 20 minutes at room temperature. The dispensed foam had a dull color, was light with airy cells. Thus, this experiment demonstrates that higher vapor pressure propellants yield stable, micro-cell foams which are preferable.

The Dymel 22:142(b) blend at a level of 4.4% by wt. with 95.6% by wt. of formulation #5 reacted in dispensing a shiny foamy surface, stable with micro-cell formation. As was experienced with the A-70 foams, it can be seen that the moisture loss was above 2.3% by wt. This compares very favorably with the A-70 propellant blend that was produced with the same formulation. The A-70 blend had a moisture weight loss of about 2.8% and was in line with the other test data.

During the manufacture of the formulation #5, the batch of foam concentrate is preferably kept warm at a temperature of from about 90–110° F. while being mixed. Without the application of heat and the mixing, the foam concentrate will be prone to hardening so that it will not flow and be unusable. Thus, it would be beneficial to modify formulation #5 in order to make the batch of foam concentrate so that it remains fluid and workable over a period of time while avoiding the need to maintain the temperature of the batch of foam concentrate in the temperature range set forth above and to subject it to constant mixing.

In this regard, the dental foam concentrate requires fluidity and lubricity compatible with its oil in water emulsion. With respect to the lubricity, polyethylene glycol (PEG) is useful for its ability to provide lubricity to the fluoride dental foam concentrate. PEG are linear polymers of ethylene oxide containing two terminal primary hydroxyl groups. The compound name PEG is usually followed by a number indicating its average molecular weight, e.g., PEG 400. Similarly, polypropylene glycol (PPG) has propylene oxide as its polymer base, with PPG 425 having a molecular weight of 425.

As the molecular weight of PEG increases, its viscosity and freezing point increase with a decrease in water solubility. The PEG 200, 300, 400 and 600 series are of particular interest for use in the invention in view of their water solubility and their use in drug and dental products. For example, U.S. Pat. No. 4,383,987 (Kiozpeoplou) shows the use of PEG 400 as a humectant in dentrifices.

In the dental fluoride foam concentrates in accordance with the invention, the PEG water soluble compounds, such as PEG 200, PEG 300, PEG 400 and PEG 600, are provided in an amount from about 1.0% to about 10.0% by weight and act as a lubricant. This lubricating property is important in the flow characteristics of the foam concentrate during production.

Although the use of a PEG water soluble compound improved the lubricity of the batch of foam concentrate, it might not always suffice to completely eliminate the need to heat and mix the batch of foam concentrate. Therefore, specially denatured alcohol (SDA) is also used in dental foam concentrates in accordance with the invention to maintain the fluidity of the foam concentrate in storage over a period of days. The amount of SDA in the foam composition is from about 2.0% to about 20.0% by weight. The use of PEG 400 together with SDA provides an unexpected synergistic reaction, better than the individual performance of the PEG 400 and SDA. Formulation #6 is such a dental foam concentrate including both PEG 400 and a specially denatured alcohol. SDA is pure ethyl alcohol or ethanol that has been denatured with a specific denaturant permitted by the Bureau of Alcohol, Tobacco and Firearms (ATF) of the U.S. Dept. of the Treasury. SDA is commercially available as 190 or 200 proof ethyl alcohol.

One particular denatured alcohol, SDA38B, is authorized for use in dentifrices, drugs and medicinal chemical products. The denaturants authorized to make specially denatured alcohol are defined by ATF, Part 212 of Title 27, Code of Federal Regulations. In most cases, denaturants must meet the quality standards of U.S. Pharmacopeia (USP) or National Formulary (NF). The denaturant is used at 1.5% with the balance of 98.5% being pure 190 or 200 proof ethyl alcohol.

Ethanol is a popular solvent which is compatible with water soluble and water insoluble compounds. In this instance, with an oil in water emulsion, the SDA38B formula is an ideal solvent in order to maintain the fluidity of the foam concentrate. When producing a flavored foam concentrate, SDA38B formula could include peppermint oil, spearmint oil, cinnamon oil or wintergreen oil as denaturants for example. If the denaturant of choice for a particular flavor is not ATF authorized, then Benzaldehyde, NF may be used. For example, if a cherry or bubblegum taste for a foam is desired, the SDA38B formula with benzaldehyde denaturant is used. This SDA38B formula has a sweet, almond-like taste that blends in well with the use of a cherry, bubblegum, grape or orange flavor base.

EXAMPLE 7
Fluoride Foam Formulation #6

| Ingredient | %/Wt. |
| --- | --- |
| Deionized water | 73.700 |
| Cetyl PO$_4$ & stearic acid | 5.500 |
| PEG 400, USP | 5.000 |
| Oleth-3 PO$_4$ | 3.000 |
| Sodium-methyl-cocoyl taurate | 1.200 |
| Cetyl alcohol, USP | 1.200 |
| Sodium monophosphate, USP | 1.000 |
| Sodium saccharin, NF | 0.600 |
| Sodium benzoate, NF | 0.100 |
| Sodium fluoride, USP | 3.000 |
| SDA38B/Spearmint/200 proof | 5.000 |
| Spearmint Flavor #FC5955 | 0.700 |
| Total: | 100.00 |

Aerosol Fill

| Item | %/Wt. | %/Wt. | %/Wt. |
| --- | --- | --- | --- |
| Formulation #5 Concentrate | 95.0 | 95.4 | 95.6 |
| Propellant A-31 | 5.0 | — | — |
| Propellant 70 | — | 4.6 | — |
| Dymel 22:142b (40:60%/wt) | — | — | 4.4 |
| Totals: | 100.0 | 100.0 | 100.0 |

TEST RESULTS
Dispensed Foam condition
Foam A-31; dull light, airy cells
Foam A-70-shiny stable, smooth microcell foam.
Foam Dymel Blend: shiny, stable microcell
Foam Weight (grams)

| Item | Foam A-31 | Foam A-70 | Dymel Foam |
| --- | --- | --- | --- |
| Initial | 1.93 | 2.53 | 3.58 |
| Ending Foam wt (g) | 1.80 | 2.46 | 3.50 |
| Moisture loss | 0.13 | 0.07 | 0.08 |
| wt % moisture loss | 7.20 | 2.80 | 2.30 |

TEST RESULTS

In this example, the role of another propellant which achieves a good stable micro-cell fluoride foam product was used. For this test, Dymel foam (HCFC 22:HCFC 142(b) (40:60% by wt.) blend was used that yields a vapor pressure of roughly 65–70 psig. The results are shown above.

As can be seen, a 5% by wt. concentration of A-31 in formulation #6 continues to show a high degree of moisture loss (7.2%) after 20 minutes at room temperature. The dispensed foam had a dull color, was light with airy cells. Thus, this experiment demonstrates that higher vapor pressure propellants yield stable, micro-cell foams which are preferable.

The Dymel 22:142(b) blend at a level of 4.4% by wt. with 95.6% by wt. of formulation #6 reacted in dispensing a shiny foamy surface, stable with micro-cell formation. As was experienced with the A-70 foams, it can be seen that the moisture loss was above about 2.3% by wt. This compares very favorably with the A-70 propellant blend that was produced with the same formulation. The A-70 blend had a moisture weight loss of about 2.8% and was in line with the other test data.

While there have been described what are presently believed to be the preferred embodiments of the invention, those skilled in the art will realize that changes and modifications can be made thereto without departing from the spirit of the invention and it is intended to claim all such changes and modifications that fall within the true scope of the invention.

I claim:

1. A foamable dental fluoride composition for forming dental foams comprising
    (a) from about 0.5 to about 10 percent by weight available dental fluoride;
    (b) from about 1.0 to about 10 percent by weight of an emulsifier, said emulsifier selected from the group consisting of cetyl phosphate and stearic acid, indeceth carboxylic acid, acid forms of ethoxylated fatty alcohols, oleth 3, oleth 5, oleth 10, oleth 20, steareth-10, celeth-20, and mixtures thereof;
    (c) from about 0.5 to about 5 percent by weight of an emulsion stabilizer, said emulsion stabilizer being selected from the group consisting of oleth-3-phosphate, oleth-10 phosphate, cetyl phosphate, PPG-10 cetyl ether phosphate, cetostearyl alcohol, stearyl alcohol, olelyl alcohol and related fatty alcohols with linear carbon chains and wax-like materials having high molecular weights, behenic acid and mixtures thereof;
    (d) from about 0.5 to about 3.0 percent by weight of a anionic or nonionic surfactant which contributes to the emulsification of the emulsifier and emulsion stabilizer in the dental foam; and
    (e) from about 1.0% to about 10.0% by weight of polyethylene glycol (PEG).

2. The foamable dental fluoride composition of claim 1, wherein the PEG is selected from a group consisting of PEG 200, PEG 300, PEG 400 and PEG 600 and mixtures thereof.

3. The foamable dental fluoride composition of claim 1, wherein the PEG is PEG 400.

4. The foamable dental fluoride composition of claim 1, further comprising from about 2.0% to about 20.0% by weight of specially denatured alcohol (SDA).

5. The foamable dental fluoride composition of claim 4, wherein the SDA is SDA 38B/190 proof.

6. The foamable dental fluoride composition of claim 4, wherein the SDA is SDA 38B/200 proof.

7. The foamable dental fluoride composition of claim 1, further comprising from about 0.5% to about 5.0% by weight of a foam stabilizer.

8. The foamable dental fluoride composition of claim 1, wherein said water soluble fluoride component is selected from the group consisting of sodium fluoride, sodium monofluoride phosphate, stannous fluoride, fluoroalkylphosphate salts, quaternary ammonium fluorides, and mixtures thereof.

9. The foamable dental fluoride composition of claim 1, wherein said emulsifier is acidic and provides said composition with a pH of from about 2.5 to about 3.5.

10. The foamable dental fluoride composition of claim 1, wherein said emulsifier comprises a combination of cetyl phosphate and stearic acid.

11. The foamable dental fluoride composition of claim 1, wherein said surfactant is selected from the group consisting of sodium N-methyl N-cocoyl taurate, sodium methyl cocoyl-N-coco-beta-aminobutyric acid, monosodium N-lauryl-1-glutamate, monosodium-N-cocoyl-1-glutamate and mixtures thereof.

12. The foamable dental fluoride composition of claim 7, wherein said foam stabilizer is selected from the group consisting of cetyl alcohol, sodium monostearate, cocoamide diethanolamine, lauramide diethanolamine, polypropylene glycol-14-butyl ether and mixtures thereof.

13. The foamable dental fluoride composition of claim 1, further comprising an aerosol propellant having a vapor pressure of from about 60 psig to about 70 psig.

14. A foamable dental fluoride composition for forming dental foams comprising
    (a) from about 0.5 to about 10 percent by weight available dental fluoride;
    (b) from about 1.0 to about 10 percent by weight of an emulsifier, said emulsifier selected from the group consisting of cetyl phosphate and stearic acid, indeceth carboxylic acid, acid forms of ethoxylated fatty alcohols, oleth 3, oleth 5, oleth 10, oleth 20, steareth-10, celeth-20, and mixtures thereof;
    (c) from about 0.5 to about 5 percent by weight of an emulsion stabilizer, said emulsion stabilizer being selected from the group consisting of oleth-3-phosphate, oleth-10 phosphate, cetyl phospate PPG-10 cetyl ether phosphate, cetostearyl alcohol, stearyl alcohol, olelyl alcohol and related fatty alcohols with linear carbon chains and wax-like materials having high molecular weights, behenic acid and mixtures thereof;
    (d) from about 0.5 to about 3.0 percent by weight of a anionic or nonionic surfactant which contributes to the emulsification of the emulsifier and emulsion stabilizer in the dental foam; and
    (e) from about 2.0% to about 20.0% by weight of specially denatured alcohol (SDA).

15. The foamable dental fluoride composition of claim 14, further comprising from about 1.0% to about 10.0% by weight of polyethylene glycol (PEG).

16. The foamable dental fluoride composition of claim 15, wherein the PEG is selected from a group consisting of PEG 200, PEG 300, PEG 400 and PEG 600 and mixtures thereof.

17. The foamable dental fluoride composition of claim 15, wherein the PEG is PEG 400.

18. The foamable dental fluoride composition of claim 14, wherein the SDA is SDA 38B/190 proof.

19. The foamable dental fluoride composition of claim 14, wherein the SDA is SDA 38B/200 proof.

20. The foamable dental fluoride composition of claim 14, further comprising from about 0.5% to about 5.0% by weight of a foam stabilizer.

21. The foamable dental fluoride composition of claim 14, wherein said water soluble fluoride component is selected from the group consisting of sodium fluoride, sodium monofluoride phosphate, stannous fluoride, fluoroalkylphosphate salts, quaternary ammonium fluorides, and mixtures thereof.

22. The foamable dental fluoride composition of claim 14, wherein said emulsifier is acidic and provides said composition with a pH of from about 2.5 to about 3.5.

23. The foamable dental fluoride composition of claim 14, wherein said emulsifier comprises a combination of cetyl phosphate and stearic acid.

24. The foamable dental fluoride composition of claim 14, wherein said surfactant is selected from the group consisting of sodium N-methyl N-cocoyl taurate, sodium methyl cocoyl-N-coco-beta-aminobutyric acid, monosodium N-lauryl-1-glutamate, monosodium-N-cocoyl-1-glutamate and mixtures thereof.

25. The foamable dental fluoride composition of claim 20, wherein said foam stabilizer is selected from the group consisting of cetyl alcohol, sodium monostearate, cocoamide diethanolamine, lauramide diethanolamine, polypropylene glycol- 1 4-butyl ether and mixtures thereof.

26. The foamable dental fluoride composition of claim 14, further comprising an aerosol propellant having a vapor pressure of from about 60 psig to about 70 psig.

* * * * *

UNITED STATES PATENT AND TRADEMARK OFFICE
CERTIFICATE OF CORRECTION

PATENT NO. : 6,251,369 B1
DATED : June 26, 2001
INVENTOR(S) : Stoltz

It is certified that error appears in the above-identified patent and that said Letters Patent is hereby corrected as shown below:

<u>Title page,</u>
Item [73], Assignee, should read -- Sultan Dental Products, Ltd --

Signed and Sealed this

Fourth Day of November, 2003

JAMES E. ROGAN
*Director of the United States Patent and Trademark Office*